United States Patent
Edwards et al.

(10) Patent No.: US 12,087,425 B2
(45) Date of Patent: *Sep. 10, 2024

(54) UTILIZING A MACHINE LEARNING MODEL TO IDENTIFY UNHEALTHY ONLINE USER BEHAVIOR AND TO CAUSE HEALTHY PHYSICAL USER BEHAVIOR

(71) Applicant: Capital One Services, LLC, McLean, VA (US)

(72) Inventors: Joshua Edwards, Philadelphia, PA (US); Michael Mossoba, Arlington, VA (US); Abdelkadar M'Hamed Benkreira, Washington, DC (US)

(73) Assignee: Capital One Services, LLC, McLean, VA (US)

( * ) Notice: Subject to any disclaimer, the term of this patent is extended or adjusted under 35 U.S.C. 154(b) by 325 days.

This patent is subject to a terminal disclaimer.

(21) Appl. No.: 17/247,230

(22) Filed: Dec. 4, 2020

(65) Prior Publication Data

US 2021/0090710 A1 Mar. 25, 2021

Related U.S. Application Data

(63) Continuation of application No. 16/425,157, filed on May 29, 2019, now Pat. No. 10,861,593.

(51) Int. Cl.
*G16H 20/30* (2018.01)
*G06N 20/00* (2019.01)
*H04L 9/40* (2022.01)

(52) U.S. Cl.
CPC .......... *G16H 20/30* (2018.01); *G06N 20/00* (2019.01); *H04L 63/101* (2013.01)

(58) Field of Classification Search
CPC ........ G16H 20/30; G16H 40/67; G16H 50/20; G06N 20/00; H04L 63/101; H04L 63/1425

See application file for complete search history.

(56) References Cited

U.S. PATENT DOCUMENTS 10,576,379 B1 * 3/2020 Wakeford ............... A63F 13/73
10,825,028 B1 * 11/2020 Kramme ............ G06Q 20/4016
(Continued)

FOREIGN PATENT DOCUMENTS

WO WO-2018017741 A1 * 1/2018 ........... G06F 16/957

OTHER PUBLICATIONS

Chou et al., Understanding online repurchase intention: social exchange theory and shopping habit, 2016, Information Systems and e-Business Management, pp. 19-45. (Year: 2016).*

(Continued)

*Primary Examiner* — Christopher L Gilligan
(74) *Attorney, Agent, or Firm* — Harrity & Harrity, LLP

(57) ABSTRACT

A device receives, from a client device, behavior data indicating an action of a user of the client device, and processes the behavior data, with a model, to determine whether the action satisfies a behavior threshold. The device determines preventative actions to perform to prevent the action of the user, when the action is determined to satisfy the behavior threshold, and performs the preventative actions to prevent the action of the user. The device provides, to the client device, a request indicating that the user perform a physical activity before the one or more preventative actions are disabled, and monitors a performance of the physical activity by the user. The device determines whether the user satisfies the performance of the physical activity based on the monitoring, and disables the one or more preventative actions when it is determined that the user satisfies the performance of the physical activity.

20 Claims, 13 Drawing Sheets

(56) References Cited

U.S. PATENT DOCUMENTS

| | | | |
|---|---|---|---|
| 10,861,593 B1 | 12/2020 | Edwards | |
| 2015/0141123 A1* | 5/2015 | Callaway | G07F 17/3209 |
| | | | 463/25 |
| 2017/0041454 A1 | 2/2017 | Nicholls et al. | |
| 2017/0148264 A1* | 5/2017 | Pichette | G06Q 20/123 |
| 2017/0189815 A1 | 7/2017 | Tweedale et al. | |
| 2017/0332951 A1* | 11/2017 | Ahmad | G16H 50/20 |
| 2018/0247241 A1 | 8/2018 | Avrahami et al. | |
| 2018/0349583 A1 | 12/2018 | Turgeman et al. | |
| 2018/0352301 A1* | 12/2018 | Tofighbakhsh | H04N 21/2668 |
| 2019/0019426 A1 | 1/2019 | Chambers | |
| 2019/0075128 A1 | 3/2019 | Roosenraad et al. | |
| 2019/0362858 A1* | 11/2019 | Valentino | G16H 40/67 |
| 2020/0111022 A1* | 4/2020 | Silberman | G06N 3/045 |
| 2020/0137097 A1 | 4/2020 | Zimmermann et al. | |
| 2020/0228612 A1* | 7/2020 | Salters | H04L 67/51 |
| 2020/0327449 A1* | 10/2020 | Tiwari | G06Q 30/0202 |

OTHER PUBLICATIONS

Blocksite., "Block Site—Block Distracting Apps & Sites," Jan. 1, 2019, 2 pages. Retrieved from Internet: [URL:https://play_google.com/store/apps/details?id=co_ blocksite&hl=en_US].

Tandon G., "Machine Learning for Host-based Anomaly Detection", Florida Institute of Technology Dissertation, May 2008, pp. 1-139.

* cited by examiner

UTILIZING A MACHINE LEARNING MODEL TO IDENTIFY UNHEALTHY ONLINE USER BEHAVIOR AND TO CAUSE HEALTHY PHYSICAL USER BEHAVIOR

RELATED APPLICATION

This application is a continuation of U.S. patent application Ser. No. 16/425,157, filed May 29, 2019 (now U.S. Pat. No. 10,861,593), which is incorporated herein by reference.

BACKGROUND

Research has shown that excessive use of technology, such as television, video games, and the Internet, creates a variety of mental and medical health issues for individuals. For example, if an individual excessively utilizes devices (e.g., computers, tablets, smart phones, televisions, etc.) to browse the Internet, perform online shopping, watch television, and/or the like, the physical health of the individual deteriorates due to the sedentary nature of such activities. Furthermore, an individual may suffer mental health issues due to technology, such as online shopping addictions, online gambling addictions, social media addictions, and/or the like.

SUMMARY

According to some implementations, a method may include receiving, from a client device, behavior data indicating an action of a user of the client device, wherein the action may be performed by the user via the client device, and wherein the action may be associated with online activity of the user via the client device. The method may include processing the behavior data, with a machine learning model, to determine whether the action satisfies a behavior threshold, wherein the behavior threshold may be associated with an online usage time of the user via the client device or a usage of an online resource by the user via the client device. The method may include determining one or more preventative actions to perform to mitigate the action of the user, wherein the one or more preventative actions may be determined based on the action and when the action is determined to satisfy the behavior threshold. The method may include performing the one or more preventative actions to mitigate the action of the user, wherein the one or more preventative actions may relate to blocking or disabling one or more functions of the client device. The method may include providing, to the client device, a request indicating that the user perform a physical activity before the one or more preventative actions are disabled, and monitoring a performance of the physical activity by the user. The method may include determining whether the user satisfies the performance of the physical activity based on monitoring the performance of the physical activity by the user, and selectively maintaining or disabling the one or more preventative actions based on whether the user satisfies the performance of the physical activity. The one or more preventative actions may be maintained when the user fails to satisfy the performance of the physical activity, and the one or more preventative actions may be disabled when the user satisfies the performance of the physical activity.

According to some implementations, a device may include one or more memories, and one or more processors, communicatively coupled to the one or more memories, to receive a machine learning model that has been trained to determine whether an action of a user satisfies a behavior threshold, wherein the behavior threshold may be associated with an online usage time of the user via a client device, or a usage of an online resource by the user via the client device. The one or more processors may receive, from the client device, behavior data indicating the action of the user, wherein the action may be performed by the user via the client device, and may process the behavior data, with the machine learning model, to determine whether the action satisfies the behavior threshold. The one or more processors may determine a preventative action to perform to prevent the action of the user, wherein the preventative action may be determined based on the action and when the action is determined to satisfy the behavior threshold. The one or more processors may perform the preventative action to prevent the action of the user, wherein the preventative action may relate to blocking or disabling one or more functions of the client device. The one or more processors may provide, to the client device, a request indicating that the user perform a physical activity before the preventative action is disabled, and may monitor a performance of the physical activity by the user. The one or more processors may determine whether the user satisfies the performance of the physical activity based on monitoring the performance of the physical activity by the user, and may maintain the preventative action when the user fails to satisfy the performance of the physical activity.

According to some implementations, a non-transitory computer-readable medium may store instructions that include one or more instructions that, when executed by one or more processors of a device, cause the one or more processors to receive, from a client device, behavior data indicating an action of a user of the client device, wherein the action may be performed by the user via the client device. The one or more instructions may cause the one or more processors to process the behavior data, with a machine learning model, to determine whether the action satisfies a behavior threshold, wherein the behavior threshold may be associated with an online usage time of the user via the client device, or a usage of an online resource by the user via the client device. The one or more instructions may cause the one or more processors to determine one or more preventative actions to perform to prevent the action of the user, wherein the one or more preventative actions may be determined based on the action and when the action is determined to satisfy the behavior threshold. The one or more instructions may cause the one or more processors to perform the one or more preventative actions to prevent the action of the user, wherein the one or more preventative actions may relate to blocking or disabling one or more functions of the client device. The one or more instructions may cause the one or more processors to provide, to the client device, a request indicating that the user perform a physical activity before the one or more preventative actions are disabled, and monitor a performance of the physical activity by the user. The one or more instructions may cause the one or more processors to determine whether the user satisfies the performance of the physical activity based on monitoring the performance of the physical activity by the user, and disable the one or more preventative actions when it is determined that the user satisfies the performance of the physical activity.

DETAILED DESCRIPTION

Figure 1A:
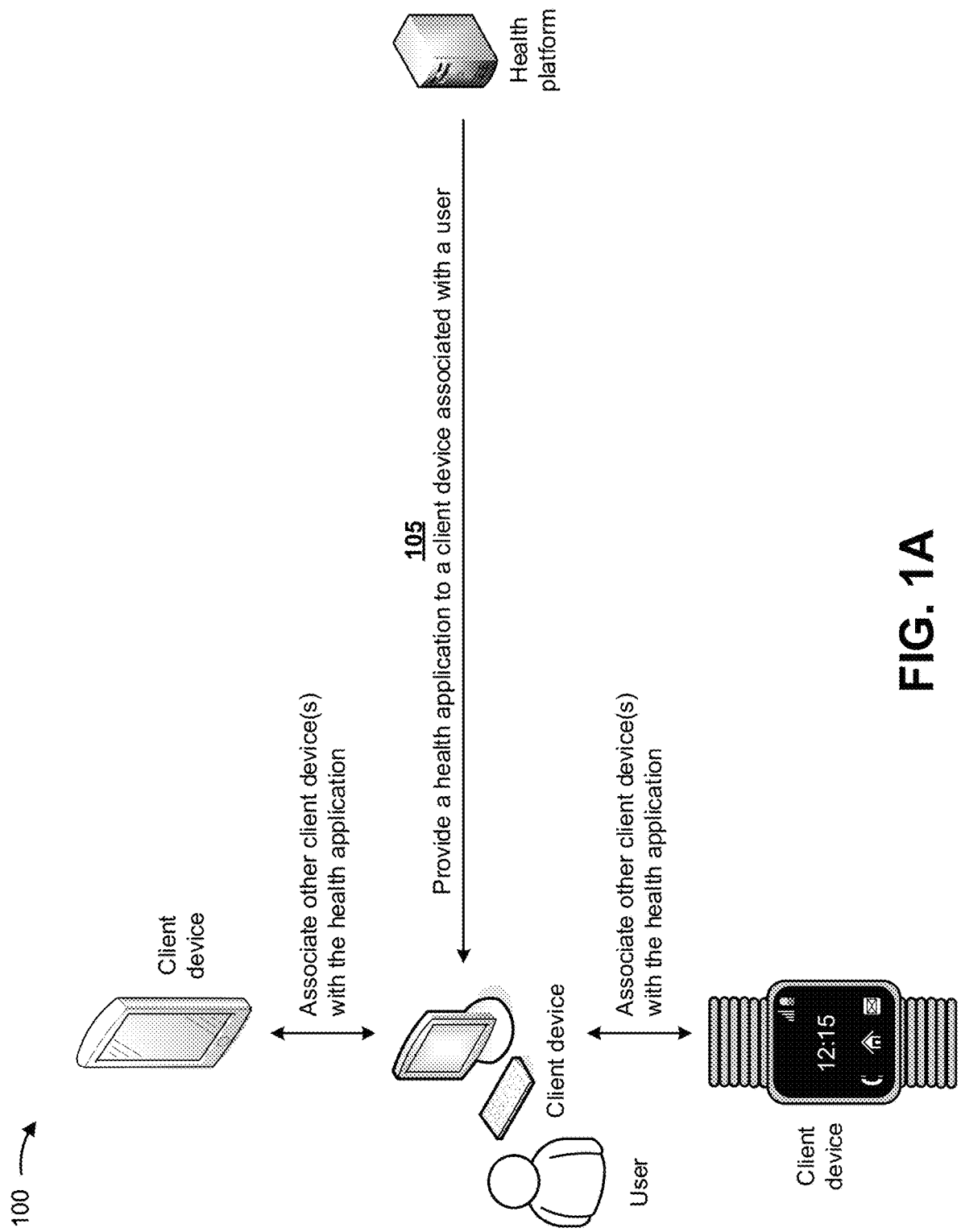
FIGS. 1A-1H are diagrams of one or more example implementations described herein.

The following detailed description of example implementations refers to the accompanying drawings. The same reference numbers in different drawings may identify the same or similar elements.

There are several costs associated with the mental and physical health issues created by excessive use of technology. For example, the mental and physical health issues waste computing resources (e.g., processing resources, memory resources, and/or the like), network resources, and human resources associated with treating mentally unhealthy individuals, treating physically unhealthy individuals, and/or the like, at doctor's offices, pharmacies, hospitals, and/or the like. Furthermore, the mental and physical health issues decrease productivity of individuals at work, which causes delays of projects and schedules at work (e.g., associated with a production of a good, a provision of a service, and/or the like). Such work delays cause computing resources and network resources to sit idle and be wasted while waiting for the delays. Finally, the mental and physical health issues require businesses to replace individuals too unhealthy to work and/or hire additional individuals to make up for lost productivity, which wastes computing resources and network resources associated with locating and hiring the replacement and/or additional individuals, as well as training those replacement and/or additional individuals.

Some implementations described herein provide a health platform that utilizes a machine learning model to identify unhealthy online user behavior and to cause healthy physical user behavior. For example, the health platform may receive, from a client device, behavior data indicating an action of a user of the client device, wherein the action may be performed by the user via the client device, and wherein the action may be associated with online activity of the user via the client device. The health platform may process the behavior data, with a machine learning model, to determine whether the action satisfies a behavior threshold, wherein the behavior threshold may be associated with an online usage time of the user via the client device or a usage of an online resource by the user via the client device. The health platform may determine preventative actions to perform to mitigate the action of the user, wherein the preventative actions may be determined based on the action and when the action is determined to satisfy the behavior threshold. The health platform may perform the preventative actions to mitigate the action of the user, wherein the preventative actions may relate to blocking or disabling one or more functions of the client device. The health platform may provide, to the client device, a request indicating that the user perform a physical activity before the preventative actions are disabled, and may monitor a performance of the physical activity by the user. The health platform may determine whether the user satisfies the performance of the physical activity based on monitoring the performance of the physical activity by the user, and may selectively maintain or disable the preventative actions based on whether the user satisfies the performance of the physical activity. The preventative actions may be maintained when the user fails to satisfy the performance of the physical activity, and the preventative actions may be disabled when the user satisfies the performance of the physical activity.

In this way, the health platform conserves computing resources and network resources that would otherwise be wasted treating mentally unhealthy individuals, treating physically unhealthy individuals, and/or the like, at doctor's offices, pharmacies, hospitals, and/or the like. Furthermore, the health platform conserves computing resources and network resources that would otherwise be wasted addressing delays of projects and schedules at work caused by mental and physical health issues of employees. Finally, the health platform conserves computing resources and network resources that would otherwise be wasted locating and hiring replacement and/or additional individuals for mentally and/or physically unhealthy employees.

FIGS. 1A-1H are diagrams of one or more example implementations 100 described herein. As shown in FIG. 1A, a client device (e.g., a stationary client device, such as desktop computer) may be associated with a health platform and a user. The user may cause the client device to request a health application from the health platform. As further shown, and by reference number 105, the health platform may provide the health application to the client device. In some implementations, the health application may enable the client device to perform functions described herein as being performed by the client device. In some implementations, and as further shown in FIG. 1A, the client device may associate other client devices (e.g., utilized by and associated with the user) with the health application, such as a mobile client device (e.g., a smart phone that includes one or more sensors), a wearable client device (e.g., a smart watch that includes one or more sensors), a television, and/or the like. In some implementations, the health platform may be associated with hundreds, thousands, millions, and/or the like of client devices and users and may provide the health application to the client devices.

Figure 1B:
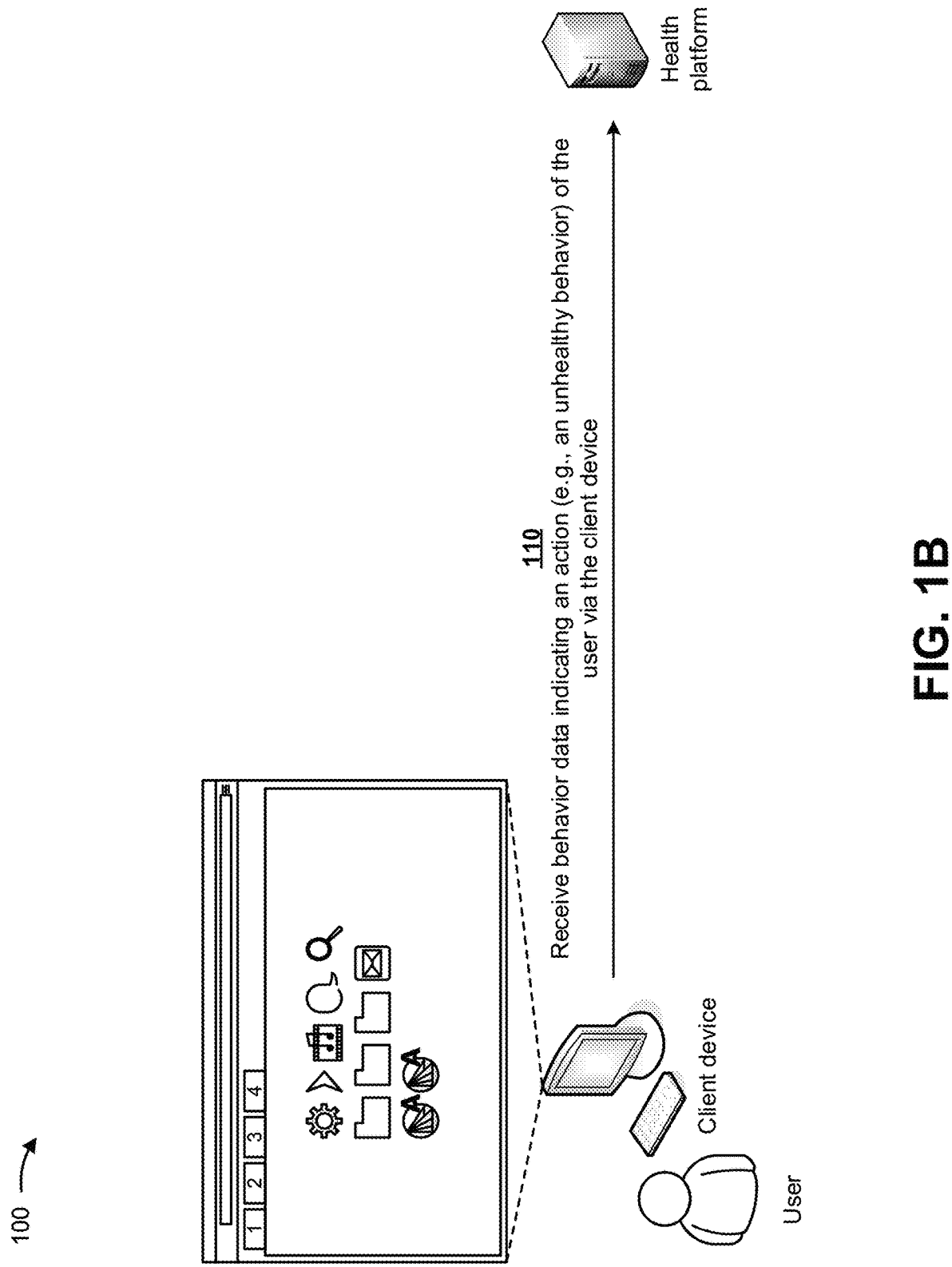

As shown in FIG. 1B, and by reference number 110, the health platform may receive, from the client device or from one of the associated client devices, behavior data indicating an action of the user via the client device or one of the associated client devices. In some implementations, the action may include an action that may be detrimental to a mental health, a physical health, a financial health, and/or the like of the user. For example, the action may include browsing the Internet, shopping online, playing a game, viewing inappropriate or indecent content, and/or the like for a period of time greater than a threshold quantity of time (e.g., minutes, one hour, two hours, and/or the like). Such actions may cause the user to be sedentary for extended periods of time (e.g., which may deteriorate the physical health of the user). In some implementations, the action may be determined based on data from one or more sensors associated with the client device and/or one or more of the associated client devices. Thus, the sensors may capture sensor data of the user, such as a heart rate of the user, a location of the user, and/or the like, and may provide the sensor data to the health application. The health application may determine behavior data based on the sensor data, and may provide the behavior data to the health platform periodically (e.g., every minute, every 5 minutes, etc.).

In another example, the action may include spending a quantity of money (e.g., greater than a threshold quantity) on in-game purchases, making online shopping purchases, making online gambling bets, and/or the like. Such actions may cause the user to be sedentary for extended periods of time (e.g., which may deteriorate the physical health of the user); may cause the user to suffer financial losses (e.g., which may be detrimental to the financial health of the user); may enable a gaming addiction, an online shopping addition, an online gambling addiction, and/or a social media addiction of the user (e.g., which may be detrimental to the mental health of the user); and/or the like.

Figure 1C:
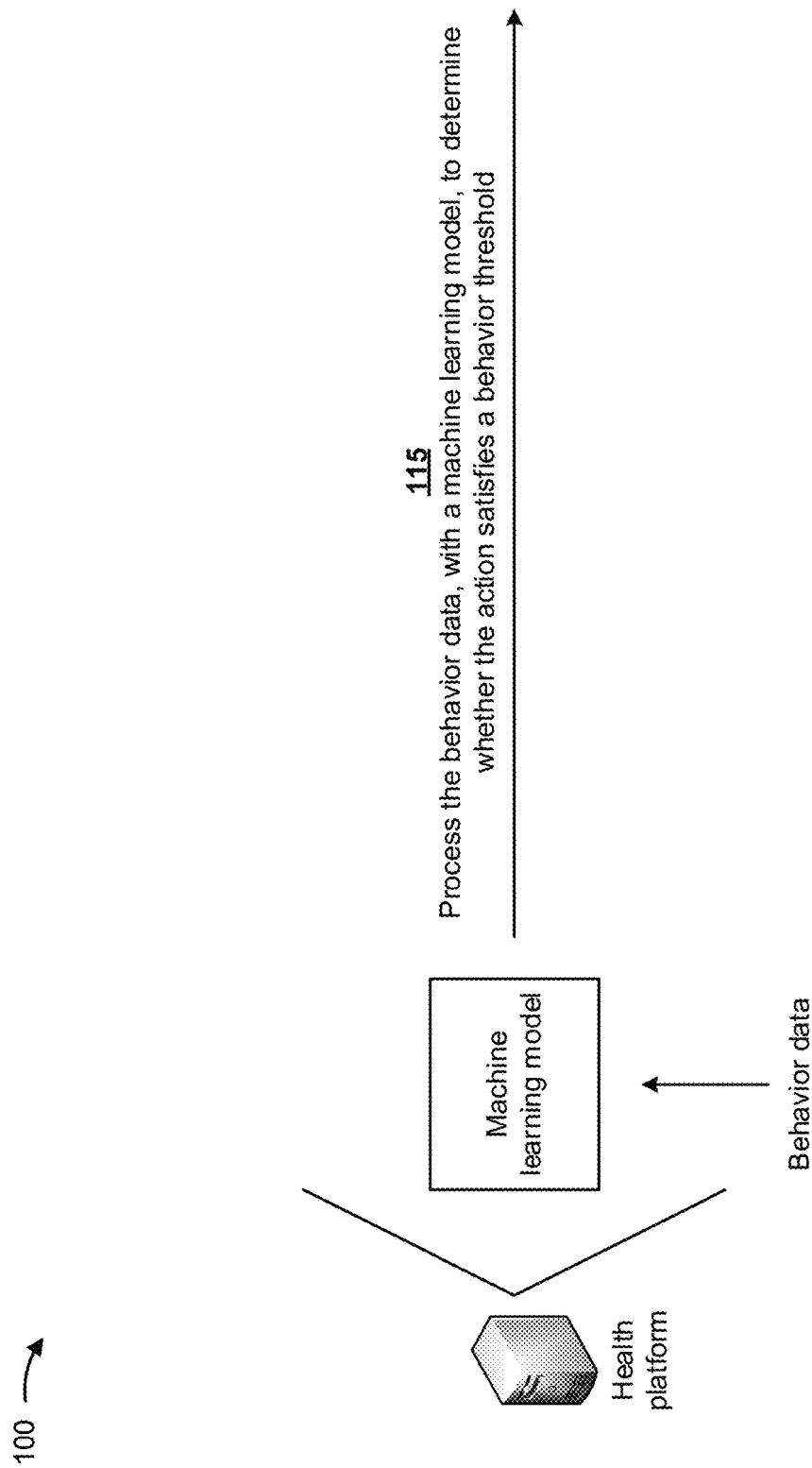

As shown in FIG. 1C, and by reference number 115, the health platform may process the behavior data, with a machine learning model, to determine whether the action satisfies a behavior threshold. In some implementations, the machine learning model may include a pattern recognition model that generates predictions indicating whether an action satisfies a behavior threshold. In some implementations, the behavior threshold may include a threshold quantity of time (e.g., one hour, two hours, and/or the like) when the action includes browsing the Internet, shopping online, playing a game, etc.; a threshold quantity of money when the action includes spending money on in-game purchases, making online shopping purchases, making online gambling bets, etc.; and/or the like. In some implementations, the machine learning model may determine whether a web site matches features of a type of web site (e.g., an online gambling web site, an online shopping web site, an online gaming web site, and/or the like) when determining whether the action satisfies the behavior threshold. Such implementations may aid the health platform in assessing an action associated with an unknown web site.

In some implementations, the health platform may perform a training operation on the machine learning model with the historical behavior data. The historical behavior data may include behavior data indicating that users browsed the Internet, shopped online, played games, etc. for a period of time greater than or less than the threshold quantity of time; behavior data indicating that users spent quantities of money (e.g., greater than or less than the threshold quantity of money) on in-game purchases, making online shopping purchases, making online gambling bets, etc.; data indicating features associated with online shopping web sites, online gambling web sites, online gaming web sites, etc.; behavior data indicating that users interacted with fields within web pages; behavior data indicating that new content was rendered on web pages (e.g., which indicates that users are navigating and selecting information provided by web pages); behavior data indicating monitored network traffic associated with the users; and/or the like.

In some implementations, the health platform may separate the historical behavior data into a training set, a validation set, a test set, and/or the like. The training set may be utilized to train the machine learning model. The validation set may be utilized to validate results generated based on training the machine learning model with the training set. The test set may be utilized to test results generated by the trained machine learning model.

In some implementations, the health platform may train the machine learning model using, for example, an unsupervised training procedure and based on the training set of the historical behavior data. For example, the health platform may perform dimensionality reduction to reduce the historical behavior data to a minimum feature set, thereby reducing resources (e.g., processing resources, memory resources, and/or the like) to train the machine learning model and may apply a classification technique to the minimum feature set.

In some implementations, the health platform may use a logistic regression classification technique to determine a categorical outcome (e.g., that actions satisfy or fail to satisfy the behavior threshold). Additionally, or alternatively, the health platform may use a naïve Bayesian classifier technique. In this case, the health platform may perform binary recursive partitioning to split the historical behavior data into partitions and/or branches and use the partitions and/or branches to perform predictions (e.g., that actions satisfy or fail to satisfy the behavior threshold). Based on using recursive partitioning, the health platform may reduce utilization of computing resources relative to manual, linear sorting and analysis of data points, thereby enabling use of thousands, millions, or billions of data points to train the machine learning model, which may result in a more accurate model than using fewer data points.

Additionally, or alternatively, the health platform may use a support vector machine (SVM) classifier technique to generate a non-linear boundary between data points in the training set. In this case, the non-linear boundary is used to classify test data into a particular class.

Additionally, or alternatively, the health platform may train the machine learning model using a supervised training procedure that includes receiving input to the machine learning model from a subject matter expert, which may reduce an amount of time, an amount of processing resources, and/or the like to train the machine learning model relative to an unsupervised training procedure. In some implementations, the health platform may use one or more other model training techniques, such as a neural network technique, a latent semantic indexing technique, and/or the like. For example, the health platform may perform an artificial neural network processing technique (e.g., using a two-layer feedforward neural network architecture, a three-layer feedforward neural network architecture, and/or the like) to perform pattern recognition with regard to optimal regions of the historical behavior data. In this case, using the artificial neural network processing technique may improve an accuracy of the trained machine learning model generated by the health platform by enabling the model to be more robust than unprocessed models to noisy, imprecise, or incomplete data, and by enabling the health platform to detect patterns and/or trends undetectable to human analysts or systems using less complex techniques.

In some implementations, the health platform may receive the trained machine learning model from another source. In such implementations, the health platform may utilize the trained machine learning model to process the behavior data and to determine whether the action satisfies the behavior threshold.

In this way, the health platform may provide the behavior data (e.g., indicating the action of the user) as an input to the machine learning model, and the machine learning model may output information indicating whether the action of the user satisfies the behavior threshold based on the input.

Figure 1D:
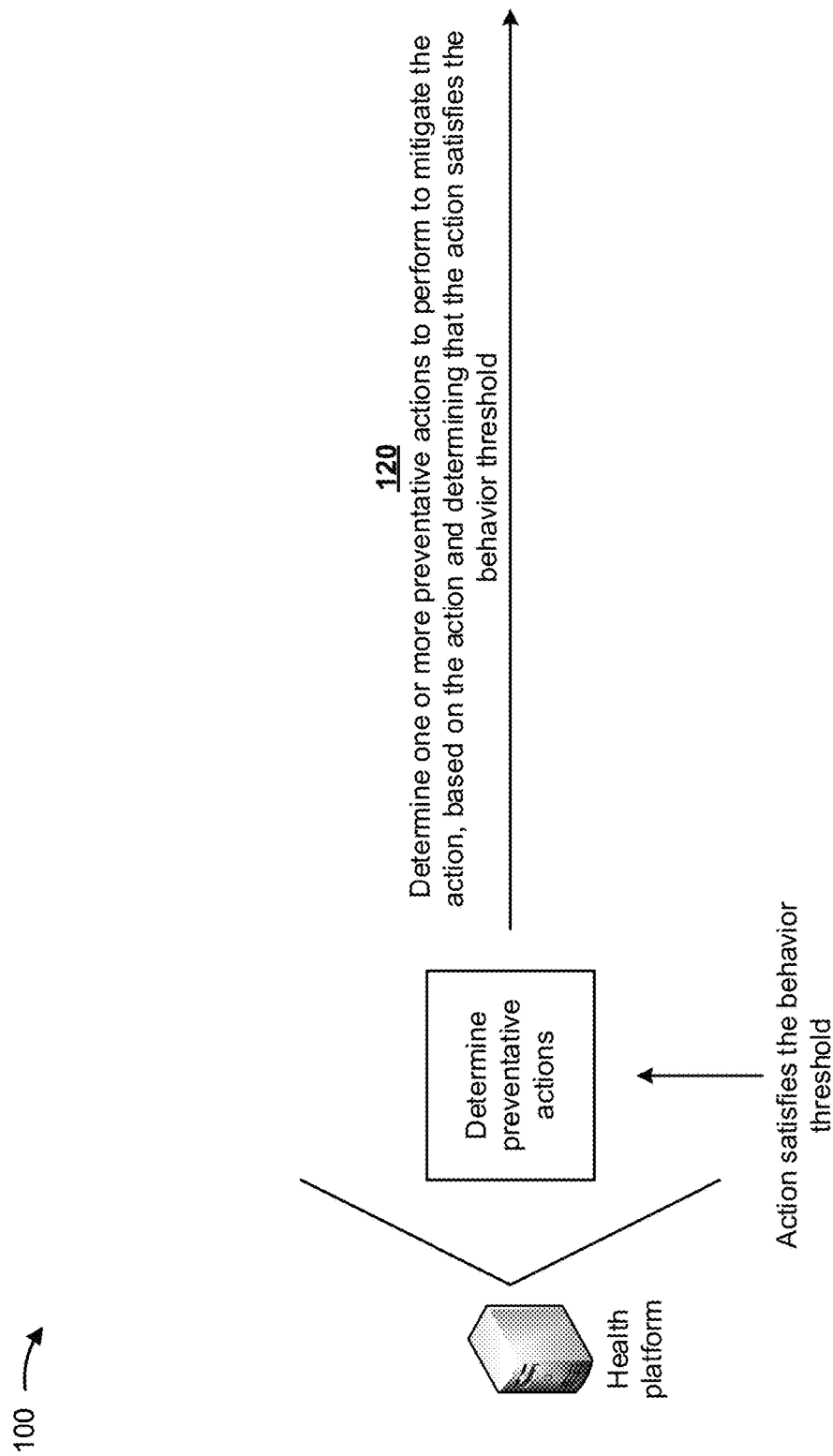

As shown in FIG. 1D, and by reference number 120, the health platform may determine one or more preventative actions to perform to mitigate the action. In some implementations, the health platform may determine the one or more preventative actions based on the action and when the health platform determines that the action satisfies the behavior threshold. If the health platform determines that the action fails to satisfy the behavior threshold, the health platform may omit determining the one or more preventative actions until the action satisfies the behavior threshold. The one or more preventative actions are described below in connection with FIG. 1E.

Figure 1E:
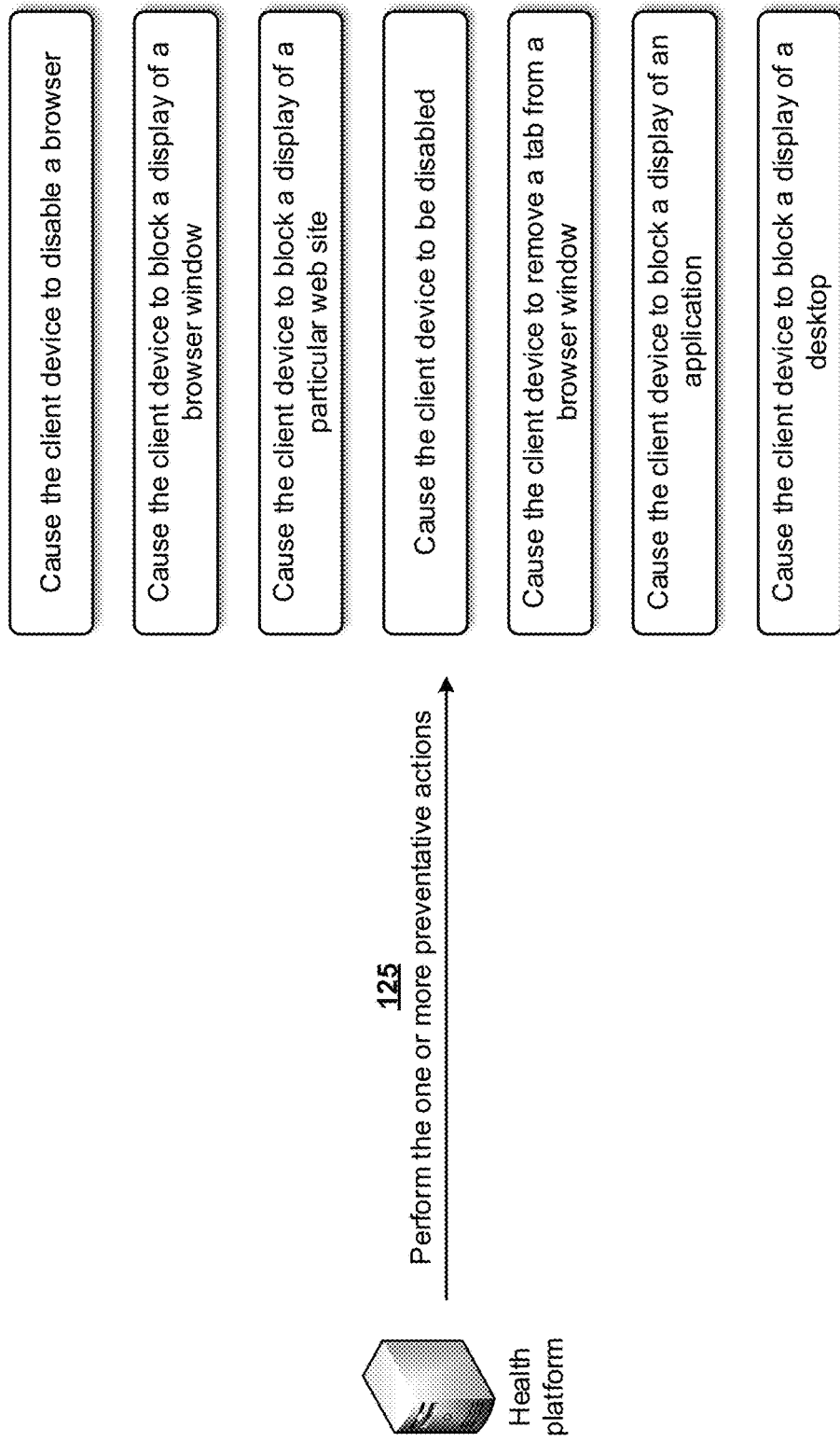

As shown in FIG. 1E, and by reference number 125, the health platform may perform the one or more preventative actions. In some implementations, the one or more preventative actions may be directed to the client device and/or the associated client devices. For example, the one or more preventative actions may include the health platform causing the client device and/or the associated client devices to disable a browser associated with the client device for a particular period of time. In this way, the health platform may prevent the user from utilizing the browser to perform the action to be prevented (e.g., browsing the Internet, online gaming, online shopping, online gambling, viewing inappropriate content, and/or the like), which may improve the health (e.g., the mental health, the physical health, the financial health, and/or the like) of the user and conserve client device computing resources and network resources.

In some implementations, the one or more preventative actions may include the health platform causing the client device and/or the associated client devices to block a display of a browser window provided by the client device. In this way, the health platform may prevent the user from performing functions associated with the browser window (e.g., viewing inappropriate web sites, utilizing online gambling web sites, utilizing online shopping web sites, and/or the like), which may improve the health of the user and conserve client device computing resources and network resources.

In some implementations, the one or more preventative actions may include the health platform causing the client device and/or the associated client devices to block a display of a particular web site (e.g., an online shopping web site, an online gambling web site, an indecent web site, and/or the like). In this way, the health platform may prevent the user from accessing the particular web site (e.g., an online shopping web site, an online gambling web site, and/or the like), which may improve the health of the user and conserve client device computing resources and network resources.

In some implementations, the one or more preventative actions may include the health platform causing the client device and/or the associated client devices to be disabled. In this way, the health platform may prevent the user from utilizing electronic devices for a period of time, which may improve the health of the user and conserve client device computing resources and network resources.

In some implementations, the one or more preventative actions may include the health platform causing the client device and/or the associated client devices to remove a tab from a browser window. In this way, the health platform may prevent the user from accessing a web site associated with the removed tab, which may improve the health of the user and conserve client device computing resources and network resources.

In some implementations, the one or more preventative actions may include the health platform causing the client device and/or the associated client devices to block a display of an application (e.g., a gaming application). In this way, the health platform may prevent the user from overutilizing the application, which may improve the health of the user and conserve client device computing resources and network resources.

In some implementations, the one or more preventative actions may include the health platform causing the client device and/or the associated client devices to block a display of a desktop. In this way, the health platform may prevent the user from overutilizing the client device and/or the associated client devices, which may improve the health of the user and conserve client device computing resources and network resources.

The above preventative actions are provided simply by way of example. The health platform may cause other preventative actions to be performed, in addition to or alternatively to the preventative actions described above. For example, the health platform may cause the client device to display a message, instructing the user to stand up and move around for a particular period of time, such as perform one or more exercises or go for a walk. In some implementations, the health platform may cause a web page (e.g., one directed to improving mental or physical health) to be displayed via the client device and/or one or more of the additional client devices.

In some implementations, additional sensor data from the client device and/or the additional client devices may indicate that the user has ignored instructions to stand up and move around. In these implementations, the health platform may cause a message to be provided or a telephone call to be placed to a user device associated with another user. For example, in the situation where the user is a child, the health platform may provide a message or place a telephone call to a parent of the child to notify the parent of the detected activity.

In some implementations, the preventative action may include disabling a transaction card associated with the user. For example, when the behavior relates to gambling or excessive online purchases, the health platform may cause further charges (e.g., to a gambling website or online store) to be blocked.

Figure 1F:
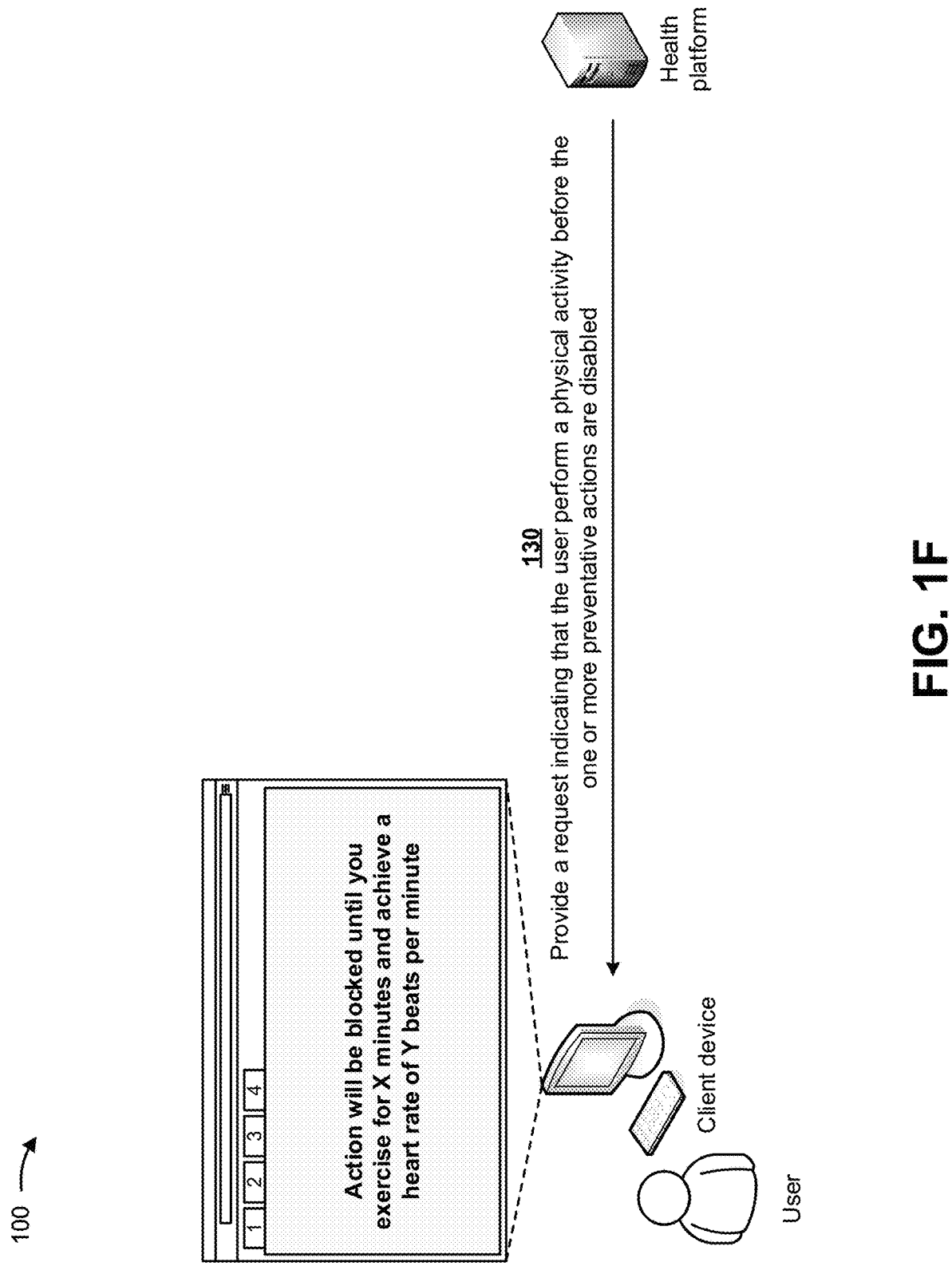

As shown in FIG. 1F, and by reference number 130, the health platform may provide, to the client device, a request indicating that the user perform a physical activity before the one or more preventative actions are disabled. In some implementations, the physical activity may include the user ceasing the action for a time period, the user performing a particular physical activity (e.g., jogging, running, walking, jumping jacks, lifting weights, etc.) for a time period, the user performing a particular physical activity until a particular heart rate of the user is achieved, the user giving the client device to another user (e.g., a parent, a wife, a husband, etc.), the user giving a transaction card to the other user, and/or the like. The client device may receive the request from the health platform and may display the request via a user interface. For example, as shown in FIG. 1F, the client device may display a user interface (e.g., blocking a desktop display of the client device) indicating that the "action will be blocked until you exercise for X minutes and achieve a heart rate of Y beats per minute."

Figure 1G:
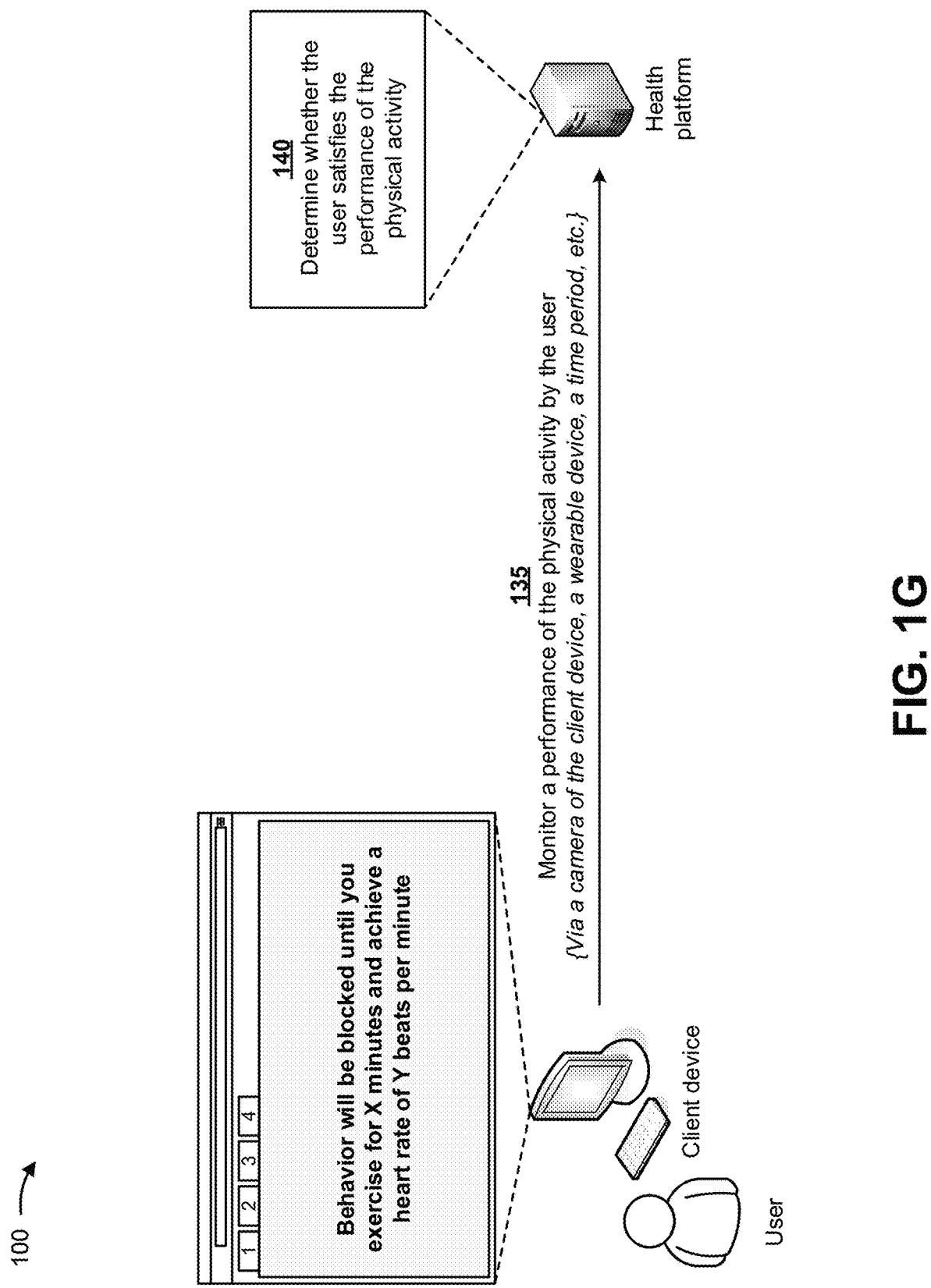

As shown in FIG. 1G, and by reference number 135, the health platform may monitor a performance of the physical activity of the user. In some implementations, the health platform may monitor the performance of the physical activity of the user by monitoring video received from a camera associated with the client device (e.g., showing the user performing the physical activity and utilizing computer vision to detect movement of the user), monitoring a wearable device worn by the user (e.g., showing a heart rate of the user, which may indicate that the user is performing the physical activity, such as exercising), monitoring a time period associated with how long the user is to perform the physical activity, monitoring notifications received from other users (e.g., indicating that the user is performing the physical activity or has performed the physical activity), monitoring interactions with the client device (e.g., filling in fields, selecting items, etc.), and/or the like. In some implementations, the health platform may monitor the physical activity of the user (e.g., when there is not physical activity) to ensure that it was appropriate to perform the one or more preventative actions (e.g., it would not be appropriate to disable a display of the client device if the user is not utilizing the display).

As further shown in FIG. 1G, and by reference number 140, the health platform may determine whether the user satisfies the performance of the physical activity. In some implementations, the health platform may determine whether the user satisfies the performance of the physical activity by determining whether the camera associated with the client device shows the user performing the physical activity (e.g., exercising), determining whether the wearable device worn by the user indicates that the user is performing the physical activity and achieved a particular heart rate, determining whether the time period associated with how long the user is to perform the physical activity has expired, determining whether notifications are received from the other users indicating that the user is performing the physical activity or has performed the physical activity, determining whether the user is interacting with the client device (e.g., filling in fields, selecting items, etc.), and/or the like. In some implementations, if the health platform determines that the user fails to satisfy the performance of the physical activity, the health platform may maintain the one or more preventative actions.

Figure 1H:
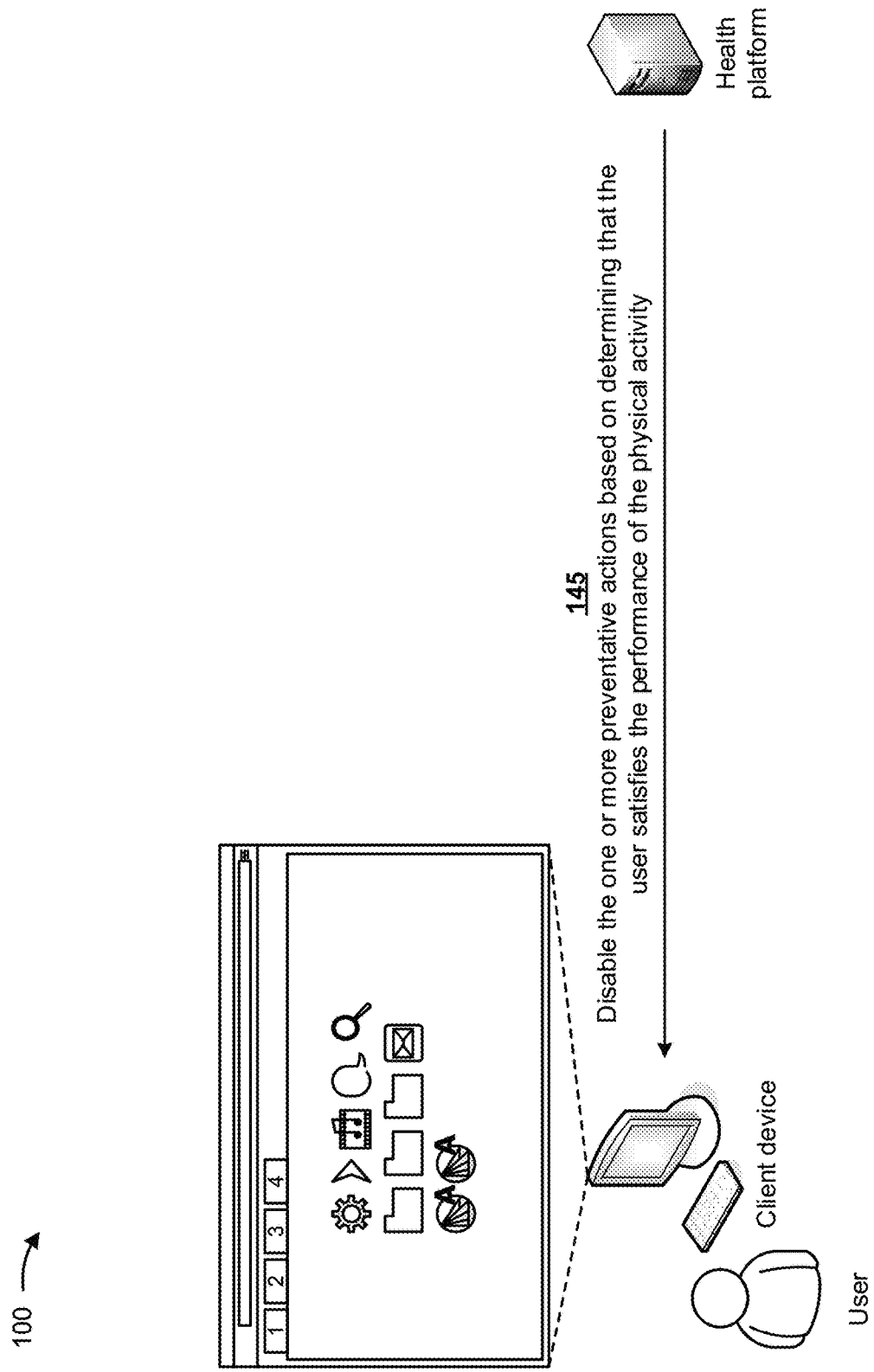

In some implementations, if the health platform determines that the user satisfies the performance of the physical activity, the health platform may disable the one or more preventative actions. As shown in FIG. 1H, and by reference number 145, the health platform may disable the one or more preventative actions based on determining that the user satisfies the performance of the physical activity. For example, based on determining that the user satisfies the performance of the physical activity, the health platform may cause the client device to remove the user interface blocking the desktop display of the client device. Therefore, the client device may provide the desktop display to the user.

In this way, several different stages of the process for identifying unhealthy online user behavior and causing healthy physical user behavior may be determined using a machine learning model, which may conserve computing resources (e.g., processing resources, memory resources, and/or the like). For example, disabling a client device when unhealthy behavior is detected conserves computing resources. Furthermore, implementations described herein use a rigorous, computerized process to perform tasks or roles that were not previously performed. For example, currently there does not exist a technique that utilizes a machine learning model to identify unhealthy online user behavior and to cause healthy physical user behavior. Further, automating the process for identifying unhealthy online user behavior and causing healthy physical user behavior conserves computing resources (e.g., processing resources, memory resources, and/or the like) that would otherwise be wasted in addressing mental health issues, physical health issues, and/or financial health issues of users.

As indicated above, FIGS. 1A-1H are provided merely as examples. Other examples may differ from what is described with regard to FIGS. 1A-1H.

Figure 2:
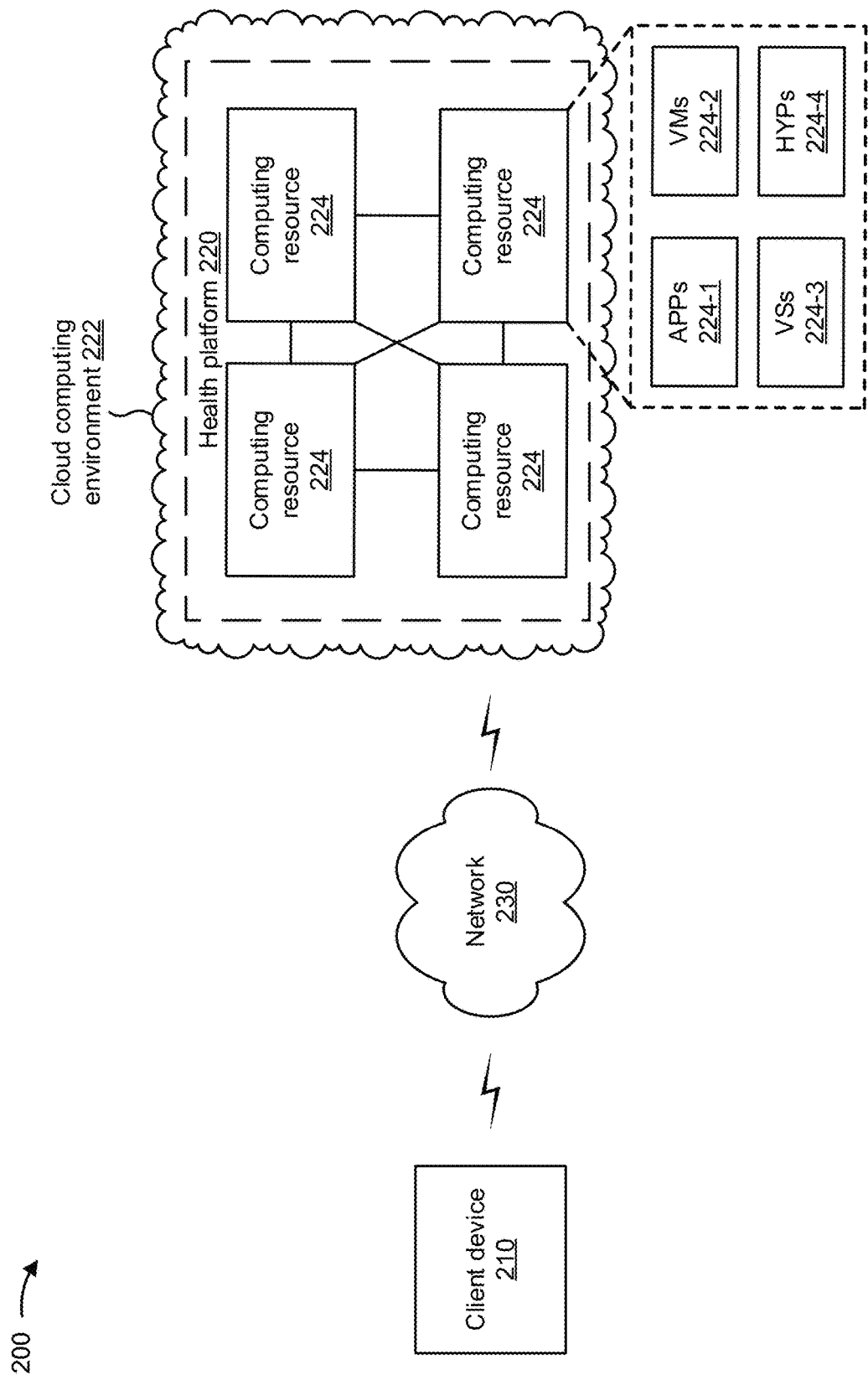
FIG. 2 is a diagram of an example environment in which systems and/or methods described herein may be implemented.

FIG. 2 is a diagram of an example environment 200 in which systems and/or methods, described herein, may be implemented. As shown in FIG. 2, environment 200 may include a client device 210, a health platform 220, and a network 230. Devices of environment 200 may interconnect via wired connections, wireless connections, or a combination of wired and wireless connections.

Client device 210 includes one or more devices capable of receiving, generating, storing, processing, and/or providing information, such as information described herein. For example, client device 210 may include a mobile phone (e.g., a smart phone, a radiotelephone, etc.), a laptop computer, a tablet computer, a desktop computer, a handheld computer, a gaming device, a wearable communication device (e.g., a smart wristwatch, a pair of smart eyeglasses, etc.), a television, or a similar type of device. In some implementations, client device 210 may receive information from and/or transmit information to health platform 220. In some implementations, client device 210 may be associated with one or more sensors. The one or more sensors may include, for example, a camera, a heart rate monitor, a motion sensor, a location sensor (e.g., a GPS sensor), and/or any other type of sensor that would aid in the identification of unhealthy physical and/or mental behavior.

Health platform 220 includes one or more devices that may utilize a machine learning model to identify unhealthy online user behavior and to cause healthy physical user behavior. In some implementations, health platform 220 may be modular such that certain software components may be swapped in or out depending on a particular need. As such, health platform 220 may be easily and/or quickly reconfigured for different uses. In some implementations, health platform 220 may receive information from and/or transmit information to one or more client devices 210.

In some implementations, as shown, health platform 220 may be hosted in a cloud computing environment 222. Notably, while implementations described herein describe health platform 220 as being hosted in cloud computing environment 222, in some implementations, health platform 220 may be non-cloud-based (i.e., may be implemented outside of a cloud computing environment) or may be partially cloud-based.

Cloud computing environment 222 includes an environment that may host health platform 220. Cloud computing environment 222 may provide computation, software, data access, storage, etc. services that do not require end-user knowledge of a physical location and configuration of system(s) and/or device(s) that host health platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host health platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by client device 210. Application 224-1 may eliminate a need to install and execute the software applications on client device 210. For example, application 224-1 may include software associated with health platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program and may support a single process. In some implementations, virtual machine 224-2 may execute on behalf of a user (e.g., a user of client device 210 or an operator of health platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may provide administrators of the storage system with flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device and/or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
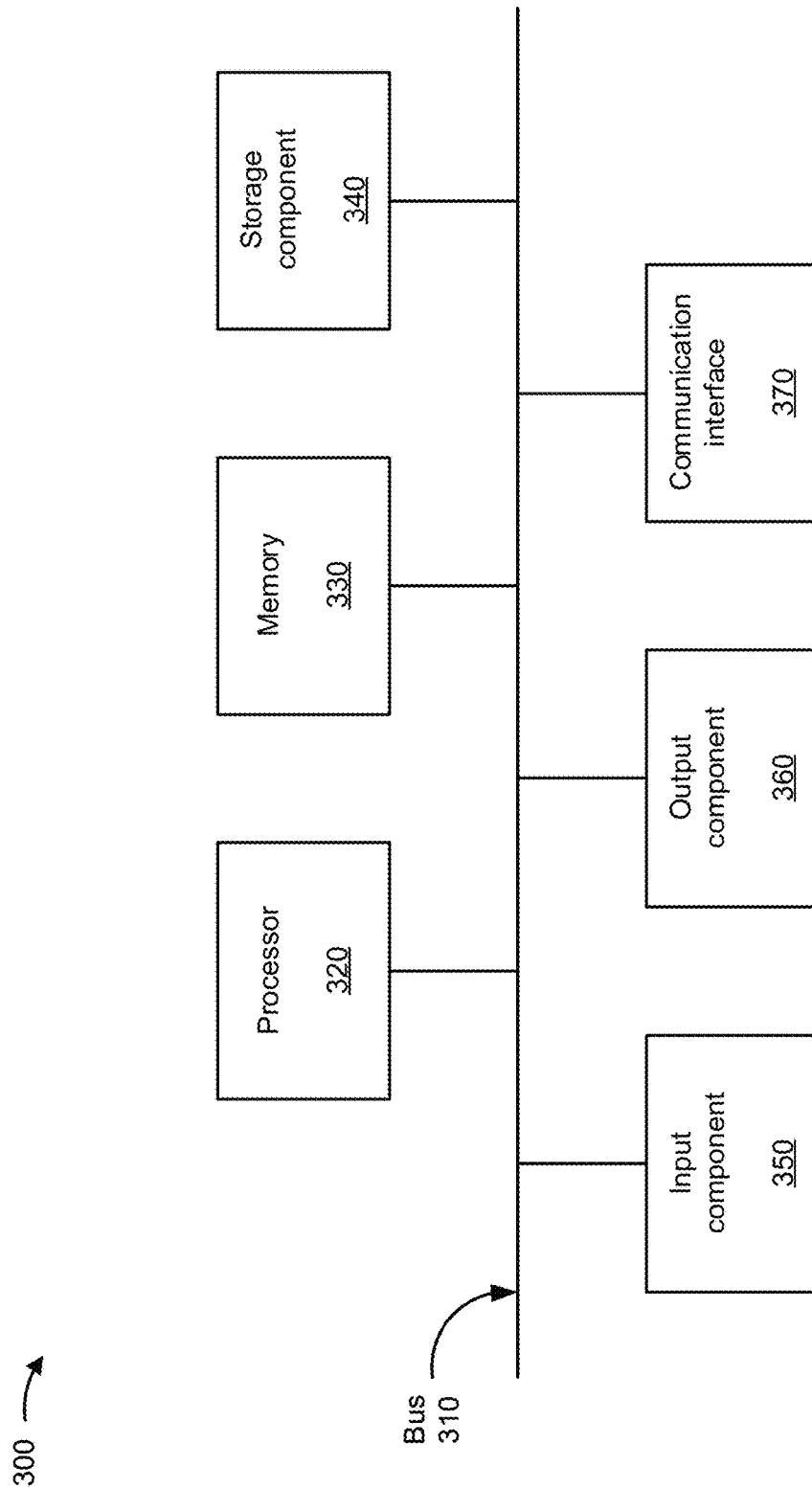
FIG. 3 is a diagram of example components of one or more devices of FIG. 2.

FIG. 3 is a diagram of example components of a device 300. Device 300 may correspond to client device 210, health platform 220, and/or computing resource 224. In some implementations, client device 210, health platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and/or a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
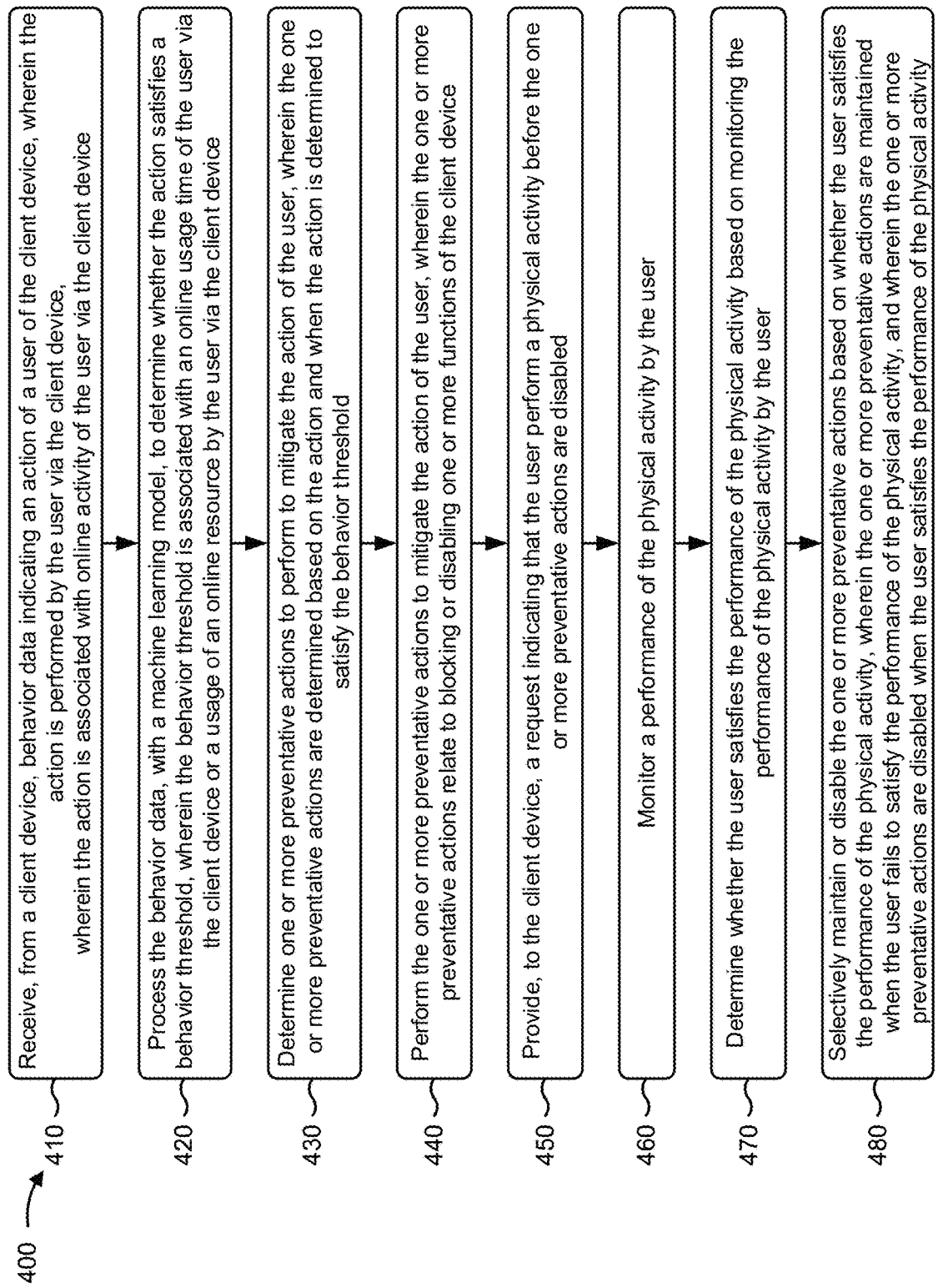
FIGS. 4-6 are flow charts of example processes for utilizing a machine learning model to identify unhealthy online user behavior and to cause healthy physical user behavior.

FIG. 4 is a flow chart of an example process 400 for utilizing a machine learning model to identify unhealthy online user behavior and to cause healthy physical user behavior. In some implementations, one or more process blocks of FIG. 4 may be performed by a health platform (e.g., health platform 220). In some implementations, one or more process blocks of FIG. 4 may be performed by another device or a group of devices separate from or including the health platform, such as a client device (e.g., client device 210).

As shown in FIG. 4, process 400 may include receiving, from a client device, behavior data indicating an action of a user of the client device, wherein the action is performed by the user via the client device, and wherein the action is associated with online activity of the user via the client device (block 410). For example, the health platform (e.g., using computing resource 224, processor 320, communication interface 370, and/or the like) may receive, from a client device, behavior data indicating an action of a user of the client device, as described above in connection with FIGS. 1A-2. In some implementations, the action is performed by the user via the client device. In some implementations, the action is associated with online activity of the user via the client device.

As further shown in FIG. 4, process 400 may include processing the behavior data, with a machine learning model, to determine whether the action satisfies a behavior threshold, wherein the behavior threshold is associated with an online usage time of the user via the client device or a usage of an online resource by the user via the client device (block 420). For example, the health platform (e.g., using computing resource 224, processor 320, memory 330, and/or the like) may process the behavior data, with a machine learning model, to determine whether the action satisfies a behavior threshold, as described above in connection with FIGS. 1A-2. In some implementations, the behavior threshold may be associated with an online usage time of the user via the client device or a usage of an online resource by the user via the client device.

As further shown in FIG. 4, process 400 may include determining one or more preventative actions to perform to mitigate the action of the user, wherein the one or more preventative actions are determined based on the action and when the action is determined to satisfy the behavior threshold (block 430). For example, the health platform (e.g., using computing resource 224, processor 320, storage component 340, and/or the like) may determine one or more preventative actions to perform to mitigate the action of the user, as described above in connection with FIGS. 1A-2. In some implementations, the one or more preventative actions may be determined based on the action and when the action is determined to satisfy the behavior threshold.

As further shown in FIG. 4, process 400 may include performing the one or more preventative actions to mitigate the action of the user, wherein the one or more preventative actions relate to blocking or disabling one or more functions of the client device (block 440). For example, the health platform (e.g., using computing resource 224, processor 320, communication interface 370, and/or the like) may perform the one or more preventative actions to mitigate the action of the user, as described above in connection with FIGS. 1A-2. In some implementations, the one or more preventative actions may relate to blocking or disabling one or more functions of the client device.

As further shown in FIG. 4, process 400 may include providing, to the client device, a request indicating that the user perform a physical activity before the one or more preventative actions are disabled (block 450). For example, the health platform (e.g., using computing resource 224, processor 320, communication interface 370, and/or the like) may provide, to the client device, a request indicating that the user perform a physical activity before the one or more preventative actions are disabled, as described above in connection with FIGS. 1A-2.

As further shown in FIG. 4, process 400 may include monitoring a performance of the physical activity by the user (block 460). For example, the health platform (e.g., using computing resource 224, processor 320, memory 330, communication interface 370, and/or the like) may monitor a performance of the physical activity by the user, as described above in connection with FIGS. 1A-2.

As further shown in FIG. 4, process 400 may include determining whether the user satisfies the performance of the physical activity based on monitoring the performance of the physical activity by the user (block 470). For example, the health platform (e.g., using computing resource 224, processor 320, storage component 340, and/or the like) may determine whether the user satisfies the performance of the physical activity based on monitoring the performance of the physical activity by the user, as described above in connection with FIGS. 1A-2.

As further shown in FIG. 4, process 400 may include selectively maintaining or disabling the one or more preventative actions based on whether the user satisfies the performance of the physical activity, wherein the one or more preventative actions are maintained when the user fails to satisfy the performance of the physical activity, and wherein the one or more preventative actions are disabled when the user satisfies the performance of the physical activity (block 480). For example, the health platform (e.g., using computing resource 224, processor 320, memory 330, communication interface 370, and/or the like) may selectively maintain or disable the one or more preventative actions based on whether the user satisfies the performance of the physical activity, as described above in connection with FIGS. 1A-2. In some implementations, the one or more preventative actions may be maintained when the user fails to satisfy the performance of the physical activity. In some implementations, the one or more preventative actions may be disabled when the user satisfies the performance of the physical activity.

Process 400 may include additional implementations, such as any single implementation or any combination of implementations described below and/or described with regard to any other process described herein.

In some implementations, when performing the one or more preventative actions, the health platform may cause the client device to be disabled. In some implementations, when performing the one or more preventative actions, the health platform may cause the client device to disable a browser associated with the client device, may cause the client device to block a display of a browser window associated with the client device, may cause the client device to block a display of a particular web site utilized by the user via the client device, may cause the client device to remove a tab from a browser window associated with the client device, may cause the client device to block a display of an application utilized by the user via the client device, and/or may cause the client device to block a display of a desktop associated with the client device.

In some implementations, the physical activity may include the user ceasing the action for a first time period, the user performing a particular physical activity for a second period, and/or the user performing the particular physical activity until a particular heart rate of the user is achieved. In some implementations, when monitoring the performance of the physical activity by the user, the health platform may monitor the performance of the physical activity via a camera associated with the client device, may monitor the performance of the physical activity via a wearable device associated with the user, and/or may monitor the performance of the physical activity via user interactions with the client device.

In some implementations, the health platform may provide, to the client device and prior to receiving the behavior data, an application to be installed on and executed by the client device, and, when receiving the behavior data, the health platform may receive the behavior data via the application. In some implementations, the user may be associated with one or more other client devices, and the health platform may perform the one or more preventative actions, on the one or more other client devices, to mitigate the action of the user.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
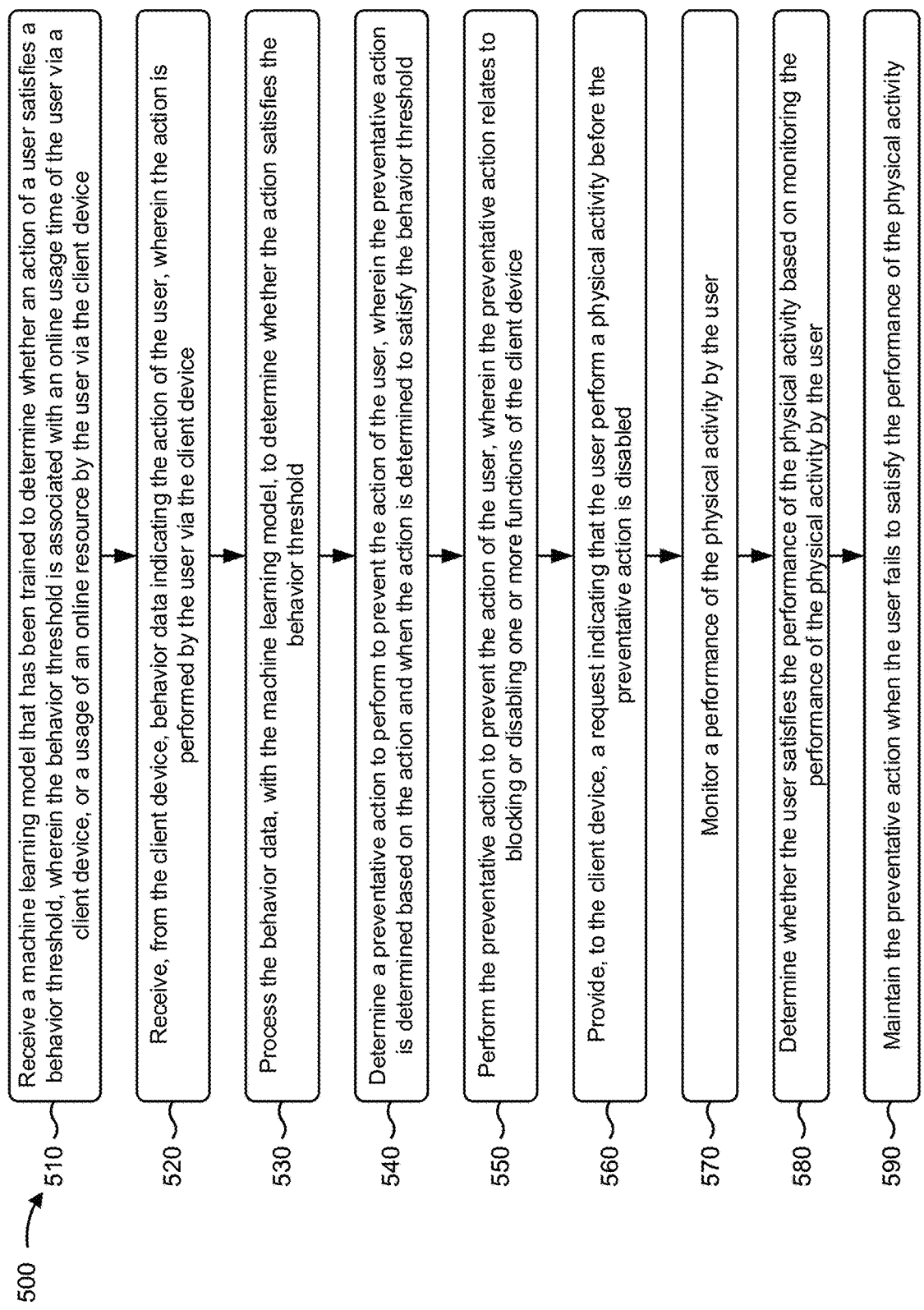

FIG. 5 is a flow chart of an example process 500 for utilizing a machine learning model to identify unhealthy online user behavior and to cause healthy physical user behavior. In some implementations, one or more process blocks of FIG. 5 may be performed by a health platform (e.g., health platform 220). In some implementations, one or more process blocks of FIG. 5 may be performed by another device or a group of devices separate from or including the health platform, such as a client device (e.g., client device 210).

As shown in FIG. 5, process 500 may include receiving a machine learning model that has been trained to determine whether an action of a user satisfies a behavior threshold, wherein the behavior threshold is associated with: an online usage time of the user via a client device, or a usage of an online resource by the user via the client device (block 510). For example, the health platform (e.g., using computing resource 224, processor 320, communication interface 370, and/or the like) may receive a machine learning model that has been trained to determine whether an action of a user satisfies a behavior threshold, as described above in connection with FIGS. 1A-2. In some implementations, the behavior threshold may be associated with an online usage time of the user via a client device, or a usage of an online resource by the user via the client device.

As further shown in FIG. 5, process 500 may include receiving, from the client device, behavior data indicating the action of the user, wherein the action is performed by the user via the client device (block 520). For example, the health platform (e.g., using computing resource 224, processor 320, communication interface 370, and/or the like) may receive, from the client device, behavior data indicating the action of the user, as described above in connection with FIGS. 1A-2. In some implementations, the action may be performed by the user via the client device.

As further shown in FIG. 5, process 500 may include processing the behavior data, with the machine learning model, to determine whether the action satisfies the behavior threshold (block 530). For example, the health platform (e.g., using computing resource 224, processor 320, storage component 340, and/or the like) may process the behavior data, with the machine learning model, to determine whether the action satisfies the behavior threshold, as described above in connection with FIGS. 1A-2.

As further shown in FIG. 5, process 500 may include determining a preventative action to perform to prevent the action of the user, wherein the preventative action is determined based on the action and when the action is determined to satisfy the behavior threshold (block 540). For example, the health platform (e.g., using computing resource 224, processor 320, memory 330, and/or the like) may determine a preventative action to perform to prevent the action of the user, as described above in connection with FIGS. 1A-2. In some implementations, the preventative action may be determined based on the action and when the action is determined to satisfy the behavior threshold.

As further shown in FIG. 5, process 500 may include performing the preventative action to prevent the action of the user, wherein the preventative action relates to blocking or disabling one or more functions of the client device (block 550). For example, the health platform (e.g., using computing resource 224, processor 320, memory 330, communication interface 370, and/or the like) may perform the preventative action to prevent the action of the user, as described above in connection with FIGS. 1A-2. In some implementations, the preventative action may relate to blocking or disabling one or more functions of the client device.

As further shown in FIG. 5, process 500 may include providing, to the client device, a request indicating that the user perform a physical activity before the preventative action is disabled (block 560). For example, the health platform (e.g., using computing resource 224, processor 320, communication interface 370, and/or the like) may provide, to the client device, a request indicating that the user perform a physical activity before the preventative action is disabled, as described above in connection with FIGS. 1A-2.

As further shown in FIG. 5, process 500 may include monitoring a performance of the physical activity by the user (block 570). For example, the health platform (e.g., using computing resource 224, processor 320, memory 330, communication interface 370, and/or the like) may monitor a performance of the physical activity by the user, as described above in connection with FIGS. 1A-2.

As further shown in FIG. 5, process 500 may include determining whether the user satisfies the performance of the physical activity based on monitoring the performance of the physical activity by the user (block 580). For example, the health platform (e.g., using computing resource 224, processor 320, storage component 340, and/or the like) may determine whether the user satisfies the performance of the physical activity based on monitoring the performance of the physical activity by the user, as described above in connection with FIGS. 1A-2.

As further shown in FIG. 5, process 500 may include maintaining the preventative action when the user fails to satisfy the performance of the physical activity (block 590). For example, the health platform (e.g., using computing resource 224, processor 320, communication interface 370, and/or the like) may maintain the preventative action when the user fails to satisfy the performance of the physical activity, as described above in connection with FIGS. 1A-2.

Process 500 may include additional implementations, such as any single implementation or any combination of implementations described below and/or described with regard to any other process described herein.

In some implementations, the health platform may disable the preventative action when the user satisfies the performance of the physical activity. In some implementations, the preventative action may include causing the client device to disable a browser associated with the client device, causing the client device to block a display of a browser window associated with the client device, causing the client device to block a display of a particular web site utilized by the user via the client device, causing the client device to be disabled, causing the client device to remove a tab from a browser window associated with the client device, causing the client device to block a display of an application utilized by the user via the client device, and/or causing the client device to block a display of a desktop associated with the client device.

In some implementations, the action may include the user utilizing the client device to access and browse the Internet for a time period, the user utilizing the client device to make online purchases that satisfy a price threshold, the user utilizing the client device to view an indecent web site, and/or the user utilizing the client device to online gamble an amount that satisfies a gambling threshold. In some implementations, the physical activity may include the user ceasing the action for a first time period, the user performing a particular physical activity for a second period, and/or the user performing the particular physical activity until a heart rate of the user is achieved.

In some implementations, when monitoring the performance of the physical activity by the user, the health platform may monitor the performance of the physical activity via a camera associated with the client device, may monitor the performance of the physical activity via a wearable device associated with the user, and/or may monitor the performance of the physical activity via user interactions with the client device. In some implementations, the health platform may provide, to the client device and prior to receiving the behavior data, an application to be installed on and executed by the client device, where the application may cause the client device to provide the behavior data to the device, and enable monitoring the performance of the physical activity by the user.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
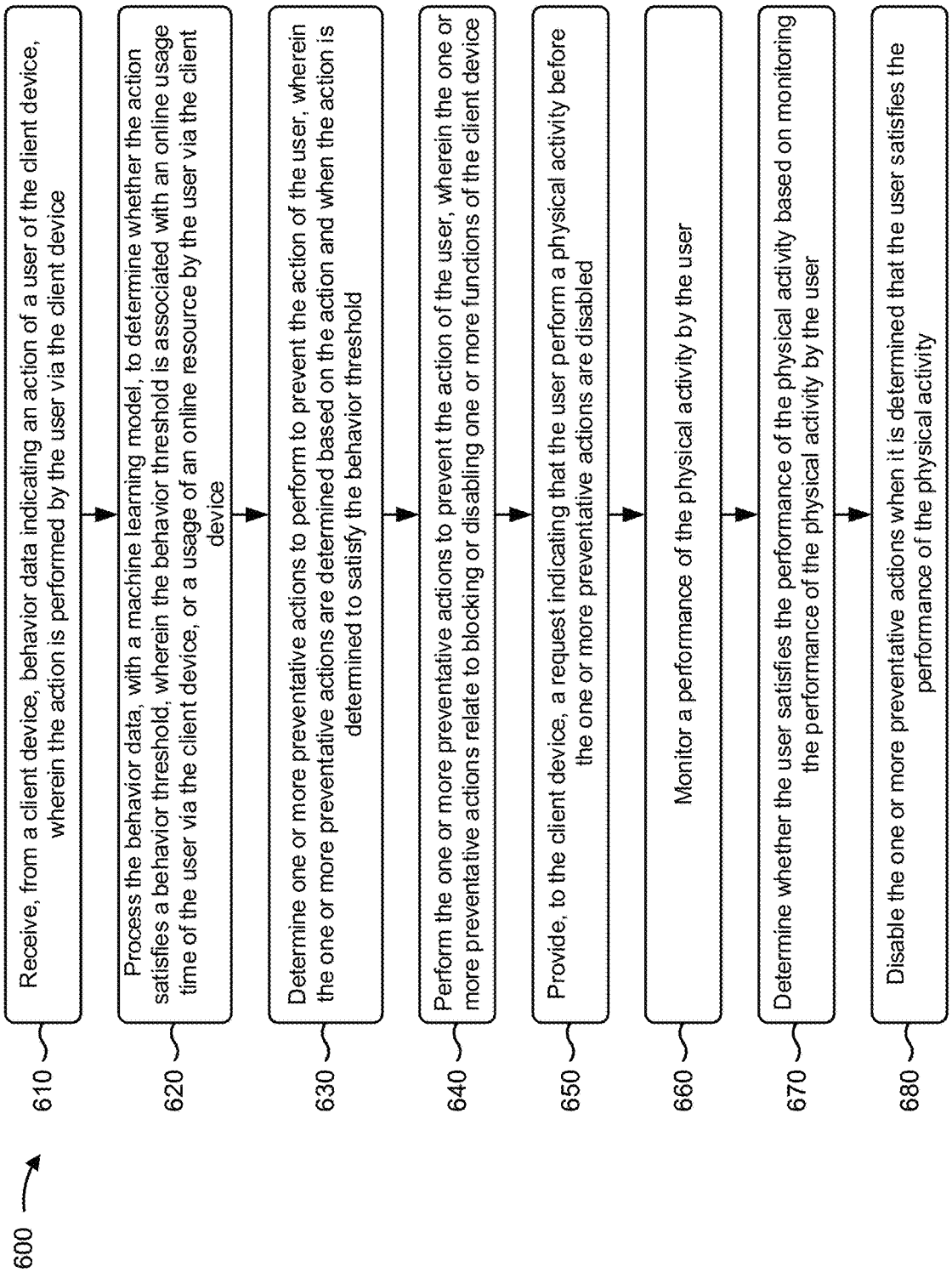

FIG. 6 is a flow chart of an example process 600 for utilizing a machine learning model to identify unhealthy online user behavior and to cause healthy physical user behavior. In some implementations, one or more process blocks of FIG. 6 may be performed by a health platform (e.g., health platform 220). In some implementations, one or more process blocks of FIG. 6 may be performed by another device or a group of devices separate from or including the health platform, such as a client device (e.g., client device 210).

As shown in FIG. 6, process 600 may include receiving, from a client device, behavior data indicating an action of a user of the client device, wherein the action is performed by the user via the client device (block 610). For example, the health platform (e.g., using computing resource 224, processor 320, communication interface 370, and/or the like) may receive, from a client device, behavior data indicating an action of a user of the client device, as described above in connection with FIGS. 1A-2. In some implementations, the action may be performed by the user via the client device.

As further shown in FIG. 6, process 600 may include processing the behavior data, with a machine learning model, to determine whether the action satisfies a behavior threshold, wherein the behavior threshold is associated with: an online usage time of the user via the client device, or a usage of an online resource by the user via the client device (block 620). For example, the health platform (e.g., using computing resource 224, processor 320, memory 330, and/or the like) may process the behavior data, with a machine learning model, to determine whether the action satisfies a behavior threshold, as described above in connection with FIGS. 1A-2. In some implementations, the behavior threshold may be associated with an online usage time of the user via the client device, or a usage of an online resource by the user via the client device.

As further shown in FIG. 6, process 600 may include determining one or more preventative actions to perform to prevent the action of the user, wherein the one or more preventative actions are determined based on the action and when the action is determined to satisfy the behavior threshold (block 630). For example, the health platform (e.g., using computing resource 224, processor 320, storage component 340, and/or the like) may determine one or more preventative actions to perform to prevent the action of the user, as described above in connection with FIGS. 1A-2. In some implementations, the one or more preventative actions may be determined based on the action and when the action is determined to satisfy the behavior threshold.

As further shown in FIG. 6, process 600 may include performing the one or more preventative actions to prevent the action of the user, wherein the one or more preventative actions relate to blocking or disabling one or more functions of the client device (block 640). For example, the health platform (e.g., using computing resource 224, processor 320, communication interface 370, and/or the like) may perform the one or more preventative actions to prevent the action of the user, as described above in connection with FIGS. 1A-2. In some implementations, the one or more preventative actions may relate to blocking or disabling one or more functions of the client device.

As further shown in FIG. 6, process 600 may include providing, to the client device, a request indicating that the user perform a physical activity before the one or more preventative actions are disabled (block 650). For example, the health platform (e.g., using computing resource 224, processor 320, communication interface 370, and/or the like) may provide, to the client device, a request indicating that the user perform a physical activity before the one or more preventative actions are disabled, as described above in connection with FIGS. 1A-2.

As further shown in FIG. 6, process 600 may include monitoring a performance of the physical activity by the user (block 660). For example, the health platform (e.g., using computing resource 224, processor 320, memory 330, communication interface 370, and/or the like) may monitor a performance of the physical activity by the user, as described above in connection with FIGS. 1A-2.

As further shown in FIG. 6, process 600 may include determining whether the user satisfies the performance of the physical activity based on monitoring the performance of the physical activity by the user (block 670). For example, the health platform (e.g., using computing resource 224, processor 320, memory 330, and/or the like) may determine whether the user satisfies the performance of the physical activity based on monitoring the performance of the physical activity by the user, as described above in connection with FIGS. 1A-2.

As further shown in FIG. 6, process 600 may include disabling the one or more preventative actions when it is determined that the user satisfies the performance of the physical activity (block 680). For example, the health platform (e.g., using computing resource 224, processor 320, memory 330, communication interface 370, and/or the like) may disable the one or more preventative actions when it is determined that the user satisfies the performance of the physical activity, as described above in connection with FIGS. 1A-2.

Process 600 may include additional implementations, such as any single implementation or any combination of implementations described below and/or described with regard to any other process described herein.

In some implementations, when performing the one or more preventative actions, the health platform may cause the client device to disable a browser associated with the client device, may cause the client device to be disabled, may cause the client device to remove a tab from a browser window associated with the client device, and/or may cause the client device to block a display of a desktop associated with the client device.

In some implementations, the action may include the user utilizing the client device to access and browse the Internet for a time period, the user utilizing the client device to make online purchases that satisfy a price threshold, the user utilizing the client device to view an indecent web site, and/or the user utilizing the client device to online gamble an amount that satisfies a gambling threshold. In some implementations, the health platform may maintain the one or more preventative actions when it is determined that the user fails to satisfy the performance of the physical activity.

In some implementations, when monitoring the performance of the physical activity by the user, the health platform may monitor the performance of the physical activity via a camera associated with the client device, may monitor the performance of the physical activity via a wearable device associated with the user, and/or may monitor the performance of the physical activity via user interactions with the client device. In some implementations, the user may be associated with one or more other client devices, and the health platform may perform the one or more preventative actions, on the one or more other client devices, to prevent the action of the user.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
receiving, by a device, historical behavior data indicating actions performed via client devices,
wherein the actions are associated with online activity comprising at least one of:
browsing the Internet,
making online gambling bets,
shopping online, or
making in-game purchases in association with playing a video game;
training, by the device and using the historical behavior data, a machine learning model to determine, based on input behavior data associated with a user:
a type of online activity associated with the input behavior data, and
data indicating whether actions identified by the input behavior data satisfy a behavior threshold associated with the type of online activity;
determining, by the device and using the machine learning model, that the actions identified by the input behavior data satisfy the behavior threshold;
providing, by the device, to a client device associated with the user, and based on the actions identified by the input behavior data satisfying the behavior threshold, an instruction that the user perform one or more exercises;
monitoring, by the device, a performance of the one or more exercises; and
causing, by the device, the client device to prevent the user from performing the actions until the user completes the performance of the one or more exercises.

2. The method of claim 1, wherein training the machine learning model comprises:
separating the historical behavior data into a training set, a validation set, and a test set;
training the machine learning model using the training set;
validating results of training the machine learning model using the validation set; and
testing the machine learning model using the test set.

3. The method of claim 1, wherein the behavior threshold is based on the type of online activity.

4. The method of claim 1, wherein the historical behavior data includes sensor data associated with the client devices, the sensor data including location data indicating a location of at least one of the client devices.

5. The method of claim 1, wherein the historical behavior data is received from a monitoring application installed on the client devices.

6. The method of claim 1, wherein the historical behavior data includes sensor data associated with the client devices, the sensor data including a heartrate of the user.

7. The method of claim 1, wherein a client device of the client devices is a stationary client device, and
wherein a subset of other client devices of the client devices are mobile client devices that are related to the client device via an application running on the client device.

8. A device, comprising:
one or more memories; and
one or more processors, communicatively coupled to the one or more memories, configured to:
receive historical behavior data indicating actions performed via client devices,
wherein the actions are associated with online activity comprising at least one of:
browsing the Internet,
making online gambling bets,
shopping online, or
making in-game purchases in association with playing a video game;
train, using the historical behavior data, a machine learning model to determine, based on input behavior data associated with a user:
a type of online activity associated with the input behavior data, and
data indicating whether actions identified by the input behavior data satisfy a behavior threshold associated with the type of online activity;
determine, using the machine learning model, that the actions identified by the input behavior data satisfy the behavior threshold;
provide, to a client device associated with the user and based on the actions identified by the input behavior data satisfying the behavior threshold, an instruction that the user perform one or more exercises;
monitor a performance of the one or more exercises; and
cause the client device to prevent the user from performing the actions until the user completes the performance of the one or more exercises for a particular time period.

9. The device of claim 8, wherein the one or more processors, when training the machine learning model, are configured to:
separate the historical behavior data into a training set, a validation set, and a test set;
train the machine learning model using the training set;
validate results of training the machine learning model using the validation set; and
test the machine learning model using the test set.

10. The device of claim 8, wherein the behavior threshold is based on the type of online spending activity.

11. The device of claim 8, wherein the historical behavior data includes sensor data associated with the client devices, the sensor data including location data indicating a location of at least one of the client devices.

12. The device of claim 8, wherein the historical behavior data is received from a monitoring application installed on the client devices.

13. The device of claim 8, wherein the historical behavior data includes sensor data associated with the client devices, the sensor data including a heartrate of the user.

14. The device of claim 8, wherein a client device of the client devices is a stationary client device, and
wherein a subset of other client devices of the client devices are mobile client devices that are related to the client device via an application running on the client device.

15. A non-transitory computer-readable medium storing a set of instructions, the set of instructions comprising:
one or more instructions that, when executed by one or more processors of a device, cause the device to:
receive historical behavior data indicating actions performed via client devices,
wherein the actions are associated with online activity comprising at least one of:
browsing the Internet,
making online gambling bets,
shopping online, or
making in-game purchases in association with playing a video game;
train, using the historical behavior data, a machine learning model to determine, based on input behavior data associated with a user:

a type of online activity associated with the input behavior data, and data indicating whether actions identified by the input behavior data satisfy a behavior threshold associated with the type of online activity;

determine, using the machine learning model, that the actions identified by the input behavior data satisfy the behavior threshold;

provide, to a client device associated with the user and based on the actions identified by the input behavior data satisfying the behavior threshold, an instruction that the user perform one or more exercises;

monitor a heart rate of the user in connection with a performance of the one or more exercises; and cause the client device to prevent the user from performing the actions until the user completes the performance of the one or more exercises.

16. The non-transitory computer-readable medium of claim 15, wherein the one or more instructions, that cause the device to train the machine learning model, cause the device to:

separate the historical behavior data into a training set, a validation set, and a test set;

train the machine learning model using the training set;

validate results of training the machine learning model using the validation set; and test the machine learning model using the test set.

17. The non-transitory computer-readable medium of claim 15, wherein the behavior threshold is based on the type of online activity.

18. The non-transitory computer-readable medium of claim 15, wherein the historical behavior data includes sensor data associated with the client devices, the sensor data including a heartrate of the user.

19. The non-transitory computer-readable medium of claim 15, wherein the historical behavior data is received from a monitoring application installed on the client devices.

20. The non-transitory computer-readable medium of claim 15, wherein a client device of the client devices is a stationary client device, and wherein a subset of other client devices of the client devices are mobile client devices that are related to the client device via an application running on the client device.

* * * * *